(12) United States Patent
Liu et al.

(10) Patent No.: US 11,208,385 B2
(45) Date of Patent: Dec. 28, 2021

(54) N-SUBSTITUTED IMIDAZOLE CARBOXYLATE COMPOUND, PREPARATION METHOD AND USE

(71) Applicant: WEST CHINA HOSPITAL, SICHUAN UNIVERSITY, Sichuan (CN)

(72) Inventors: Jin Liu, Sichuan (CN); Jun Yang, Sichuan (CN); Wensheng Zhang, Sichuan (CN); Bowen Ke, Sichuan (CN); Lei Tang, Sichuan (CN); Bin Wang, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 172 days.

(21) Appl. No.: 16/488,484

(22) PCT Filed: Jan. 31, 2018

(86) PCT No.: PCT/CN2018/074715
§ 371 (c)(1),
(2) Date: Oct. 23, 2019

(87) PCT Pub. No.: WO2018/153228
PCT Pub. Date: Aug. 30, 2018

(65) Prior Publication Data
US 2020/0231546 A1    Jul. 23, 2020

(30) Foreign Application Priority Data
Feb. 24, 2017 (CN) .......................... 201710101619.5

(51) Int. Cl.
C07D 233/90    (2006.01)
(52) U.S. Cl.
CPC .................... C07D 233/90 (2013.01)
(58) Field of Classification Search
CPC .................................................. C07D 233/90
See application file for complete search history.

(56) References Cited

FOREIGN PATENT DOCUMENTS

| CN | 102046607 A | 5/2011 |
| CN | 102548964 A | 7/2012 |
| CN | 107382870 A | 11/2017 |
| CN | 107652239 A | 2/2018 |

OTHER PUBLICATIONS

Translation of CN 107382870, Nov. 24, 2017.*

* cited by examiner

Primary Examiner — Rebecca L Anderson
(74) Attorney, Agent, or Firm — Novick, Kim & Lee, PLLC; Allen Xue

(57) ABSTRACT

An N-substituted imidazole carboxylate compound is of formula (I). In formula (I), C* is an R-type chiral carbon atom, $R_1$ and $R_2$ are independently selected from H, methyl, ethyl, cyclopropyl, cyclobutyl or isopropyl, or $R_1$ and $R_2$ form a $C_{2-5}$ alkylenyl group; $R_3$ is a substituted or unsubstituted $C_{1-18}$ saturated or unsaturated aliphatic hydrocarbon or aromatic hydrocarbon, in which the aliphatic hydrocarbon comprises a straight chain, branched chain or cyclic aliphatic hydrocarbyl. The compound or pharmaceutically acceptable salts thereof can be used to prepare central inhibitory drugs that exert sedative, hypnotic and/or anesthetic effects on humans or animals, and can produce rapid and reversible anesthetic effects, and can be rapidly metabolized into an inactive etomidate acid, and after drug withdrawal, the wake-up quality is good; and the body's corticosteroid function can be rapidly recovered after a single administration or continuous administration.

(I)

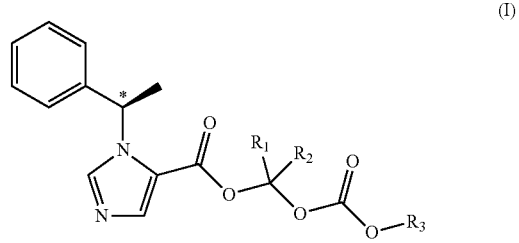

12 Claims, 1 Drawing Sheet

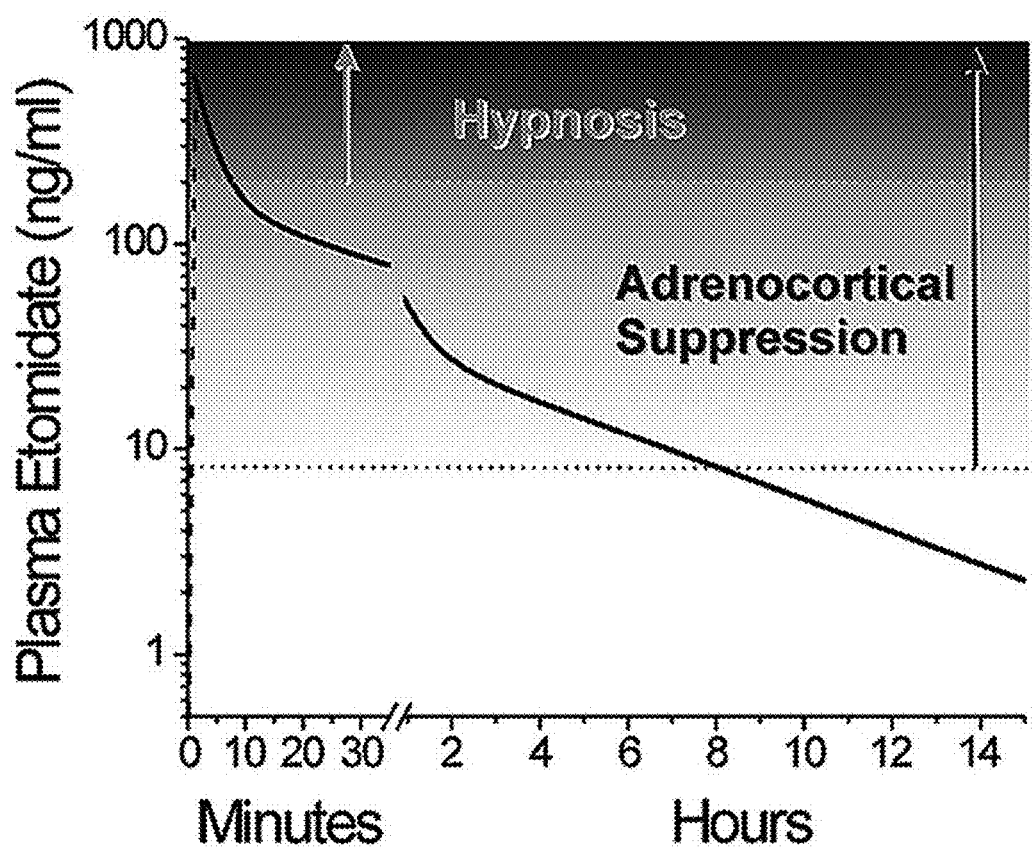

N-SUBSTITUTED IMIDAZOLE CARBOXYLATE COMPOUND, PREPARATION METHOD AND USE

TECHNICAL FIELD

The present invention relates to a N-substituted imidazole carboxylate compound characterized by producing short-acting anaesthetic effects and rapid recovery after drug withdraw, the preparative method and the uses thereof.

BACKGROUND ART

Etomidate is a general intravenous anesthesia drug marketed for a long time. Since it shows a rapid effect and the hold time is short, etomidate is an ideal drug inducing the general intravenous anesthesia. Meanwhile, due to the specific pharmacologic feature of having a good cardiovascular stability, and during anesthesia, the inhibition on body's circulation is the minimum in general anesthetics used in clinical now, thus it especially suitable for the patients with cardiac dysfunction and the aged patients undergoing a surgery (Bovill J G. 2006; Passot S et al. 2005). At present, the mechanism of anesthetic action for etomidate has already been clear, and it produces anesthetic action mainly by combining with central inhibitory receptor, $GABA_A$ receptor, and makes the receptor more sensitive to the inhibitory neurotransmitter GABA. But the further research gradually shows that etomidate has an inhibitory effect on the synthesis of body's cortical hormones, and especially for a long-time continuous infusion, the inhibition on cortical hormones is obvious and long. Since the self-synthesis of cortical hormones is an important factor for body's anti-inflammatory, the inhibition of etomidate on cortical hormones is disadvantageous for the recovery of postoperative patients, and the disadvantageous effect has already been gradually verified by clinical studies (Watt I and Ledingham I M. 1984; McKee J I and Finlay W E. 1983; Albert S G et al 2011), and even leads to the high mortality in patients, that makes the utilization of etomidate to be gradually reduced as the deep understanding, thus medical staff do not hope that the patients receiving etomidate are faced with the risk of infection increasing during postoperative recovery.

The inhibition of etomidate on cortical hormones is realized by suppressing the activity of 11-β hydroxylase, and this enzyme is a key enzyme for the synthesis of cortical hormones. This adverse effect of etomidate is related to the imidazole structure in the drug molecule, and one N atom in the imidazole ring can complex with the topological iron atom in 11-β hydroxylase, thus strengthen the combination of drug molecules and enzyme molecules, producing the inhibitory effect on 11-β hydroxylase. Moreover, the combining capacity of etomidate and 11-β hydroxylase is 100 times stronger than that of it and $GABA_A$ receptor (J. F. Cotton et al. 2009), and thus resolving the problem by improving the selectivity of receptors is very hard.

Etomidate is mainly metabolized in liver, and as the progress of drug metabolism research, the time/effect curve of therapeutic effect and adverse effect for etomidate has already been drawn (Stuart A. Forman. 2011), as shown in FIG. 1. According to FIG. 1, it can be shown that after single injection of 3 mg/kg etomidate, the minimum effective concentration producing anaesthetic effect in plasma is 200 ng/mL, and the time of maintaining the drug concentration of >200 ng/mL in plasma is only 8 minutes. While the minimum effective concentration for etomidate to inhibit the synthesis of cortical hormones is 8 ng/mL, and the time of maintaining the drug concentration of >8 ng/mL in plasma is 8 hours. These data indicate that after anesthetic dosage of etomidate is administrated to the patients, the anaesthetic effect is rapidly lost, but the inhibition on the synthesis of cortical hormones would remain for a longer time.

Based on above mention, some researchers suggest that the soft drug design method can be used to modify the structure of etomidate, and increase the metabolic rate after drug withdrawal. As a result, the blood drug level of the prototype is rapidly reduced after drug discontinuance, that is beneficial for the recovery of synthesis capability of body's cortical hormone. Among the first generation of soft drugs obtained according to this way, MOC-ET is the represent (Chinese patent CN 102046607A), and although this drug can be rapidly metabolized, its metabolite MOC-ECA itself has certain inhibitory activity against cortical hormones and the nerve center, that lead to the poor wake quality after drug withdrawal, and the inhibition on cortical hormones is not obviously relieved (Ge R L et al. 2012; Pejo E et al. 2012); In addition, the potency of MOC-ET is low, only ⅕ of etomidate (J. F. Cotton et al. 2009). Thus, the druggability of MOC-ET is poorer. Subsequently, based on above mentioned, the second generation soft drug of etomidate such as CPMM is designed and synthesized, with a potency close to etomidate, and its metabolic rate is fast, and the recovery rate is rapid after drug withdrawal, but the inhibitory action on body's cortical hormones is still obvious during continuous administration, that can be fully restored 3 hours after discontinuation of CPMM (Campagna J A et al. 2014). The metabolite of CPMM is CPMM-ECA, that has a very weak inhibitory effect on the nerve center (Ervin Pejo et al. 2016), but there is no direct research result showing whether it has inhibitory effect on cortical hormones. Continual infusion of CPMM can still affect the wake quality, and especially after administration of CPMM, the incidence rate of muscle tremor is even much higher than that of etomidate. The structures of etomidate, MOC-ET, CPMM, together with their decomposition products, are as follows:

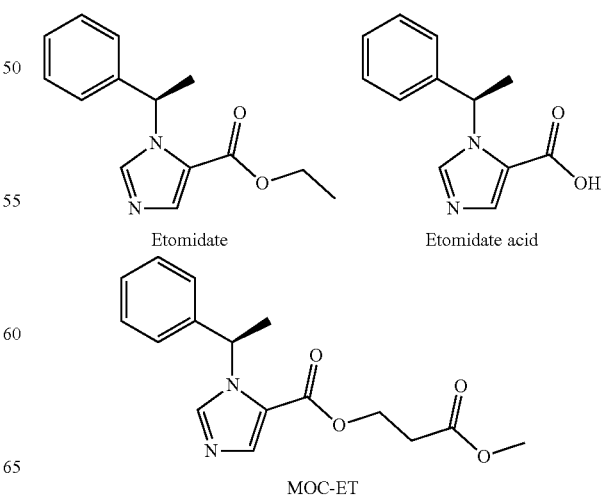

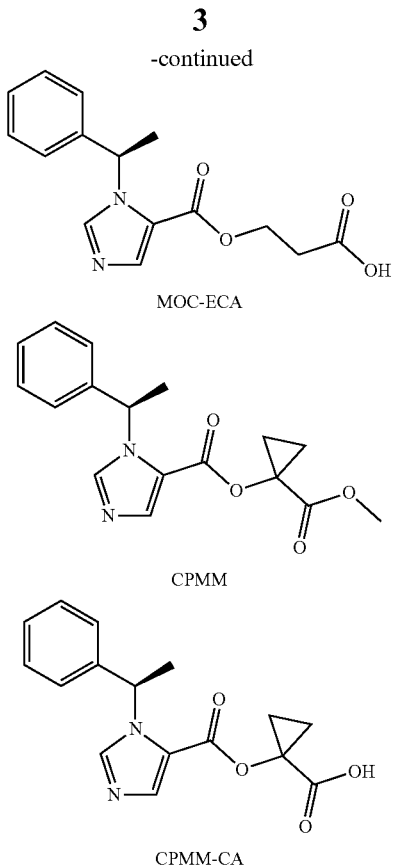

MOC-ECA

CPMM

CPMM-CA

Thus, the ideal soft drug of etomidate being capable of resolving above problems is still one of subjects to be researched.

CONTENT OF THE INVENTION

Aiming directly at above problems, the present invention provides a new soft drugs of etomidate, i.e. N-substituted imidazole carboxylate compounds that can be able to have short-acting anesthetic action and rapid recovery, and comparing with CPMM or etomidate, after single injection or continuous infusion, recovery is more rapid, and the wake quality is better, the function of body's cortical hormones can be quickly recovered, and once administrated to the animals, the incidence rate of muscle tremor is low during anesthesia or postanesthesia. Based on the above, the present invention also provides the preparative method of said compounds, and the uses of this type of compounds in the preparation of central inhibitory drugs that exert sedative, hypnotic and/or anaesthetic effects on humans or animals.

N-substituted imidazole carboxylate compounds of the present invention with short-acting anaesthetic effects and rapid recovery, having the structure of formula (I):

In formula (I), C* is an R-type chiral carbon atom, $R_1$ and $R_2$ can be independently selected from H, methyl, ethyl, cyclopropyl, cyclobutyl or isopropyl, or $R_1$ and $R_2$ form a $C_{2-5}$ alkylenyl group; $R_3$ is a substituted or unsubstituted $C_{1-8}$ saturated or unsaturated aliphatic hydrocarbon or aromatic hydrocarbon, and said aliphatic hydrocarbon comprises a straight chain, branched chain or cyclic aliphatic hydrocarbyl; the substituents in $R_3$ include but not limited to halogen, nitro or aryl.

For example, N-substituted imidazole carboxylate compounds according to the present invention can include but not limited to the following detailed compounds:

In formula (I), $R_1$ is hydrogen, $R_2$ is hydrogen, $R_3$ can be methyl, ethyl, n-propyl, isopropyl, isobutyl, sec-butyl, tert-butyl, neopentyl, cyclobutyl, 3-methyl-2-butyl, phenyl or p-bromophenyl; or In formula (I), $R_1$ and $R_2$ form ethylene, $R_3$ is methyl, ethyl, isopropyl; or In formula (I), $R_1$ is methyl, $R_2$ is hydrogen, $R_3$ is methyl, ethyl, isopropyl or sec-butyl; or In formula (I), $R_1$ is methyl, $R_2$ is methyl, $R_3$ is methyl, ethyl, isopropyl; or In formula (I), $R_1$ is ethyl, $R_2$ is hydrogen, $R_3$ is methyl, ethyl, isopropyl; or In formula (I), $R_1$ is isopropyl, $R_2$ is hydrogen, $R_3$ is methyl, ethyl, isopropyl; or In formula (I), $R_1$ is cyclopropyl, $R_2$ is hydrogen, $R_3$ is methyl, ethyl, isopropyl; or In formula (I), $R_1$ is cyclobutyl, $R_2$ is hydrogen, $R_3$ is methyl, ethyl, isopropyl; or In formula (I), $R_1$ is hydrogen, $R_2$ is hydrogen, $R_3$ is difluoroethyl, hexafluoroisopropyl, trifluoroethyl or nitroethyl; or In formula (I), $R_1$ is hydrogen, $R_2$ is hydrogen, $R_3$ is 2-methyl-3-buten-2-yl or isopentenyl.

Except for above-mentioned N-substituted imidazole carboxylate compounds of formula (I), N-substituted imidazole carboxylate compounds according to the present invention with short-acting anaesthetic effects and rapid recovery further include pharmaceutically acceptable salts of compounds of formula (I). Amongst, sulfonates or hydrochlorates and so on formed from compounds of formula (I) can be preferable.

For the basic preparative method of N-substituted imidazole carboxylate compounds of formula (I) according to the present invention, using N-substituted imidazole carboxylic compounds of formula (II) and halogenated compounds of formula (III) as starting materials, the substitution reaction is carried out at the presence of inorganic bases including potassium carbonate, cesium carbonate, or organic bases including triethylamine, 1,8-diazabicycloundec-7-ene (DBU). The reaction procedure is as follows:

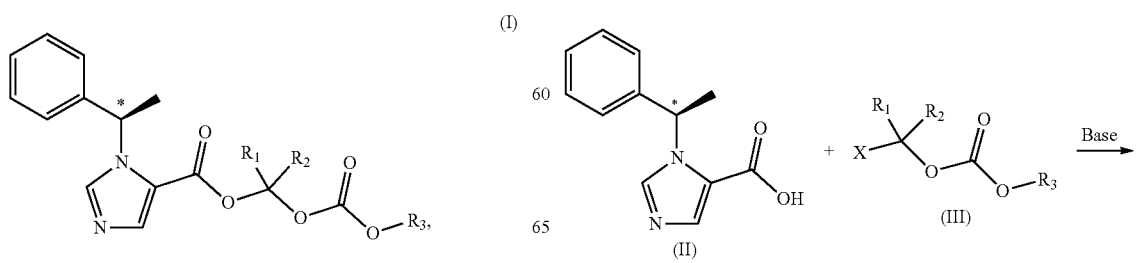

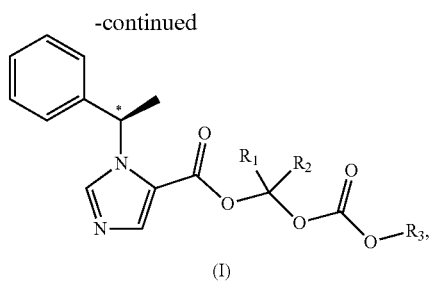

In the structures of reactants, $R_1$, $R_2$, and $R_3$ are same as those mentioned above, respectively; X is halogen substituents, and generally chlorine can be preferable.

Wherein, when $R_1$ and $R_2$ form alkylenyls, the preparative method can also use the reaction of N-substituted imidazole carboxylate compounds of formula (IV) and chloroformate compounds of formula (V) to obtain the target compounds of formula (I). The reaction procedures are as follows:

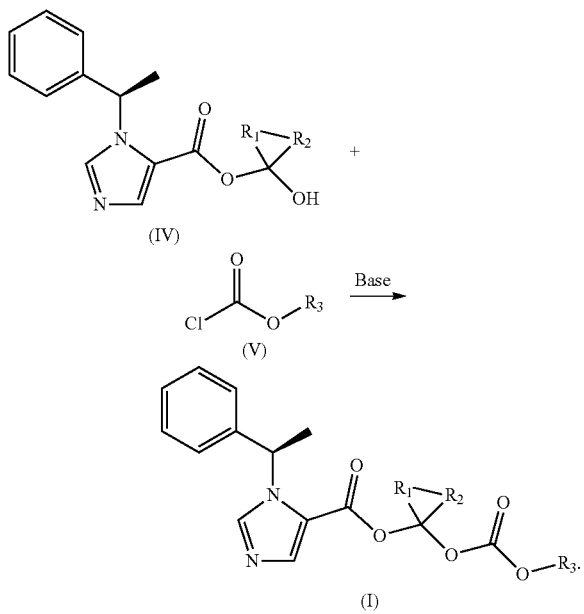

In general, it is more beneficial for said reaction to be carried out in polar aprotic solvents. For example, said reaction can be carried out in the polar aprotic solvents that include but not limited to common-used N,N-dimethylformamide (DMF), dimethylsulfoxide (DMSO) or acetonitrile, etc.

Said pharmaceutically acceptable salts of compounds of formula (I) can be obtained after removal of solvents by routine ways, such as after compound of formula (I) is dissolved in alcohol or ester solvents, to which is then added the calculated amount of acid and mixed to form salts. Wherein, preferably, the salts include but not limited to corresponding sulfonates or hydrochlorides formed by sulfonic acid or hydrochloric acid, etc., via routine ways.

Animal experiment indicates that the compound with the structure of formula (I) or pharmaceutically acceptable salts thereof are both characterized by producing rapid effects, the good wake-up quality, the rapid recovery of body's corticosteroid function after a single administration or continuous administration, and the low incidence of muscle tremors in body during administration and after drug withdrawal, and obviously reduce the side effects of etomidate. For example, comparative experiment shows that compounds of the present invention can be rapidly disintegrated under the action of liver homogenate of rats, while the control drug etomidate is slowly decomposed, suggesting that compounds of the present invention are characterized by rapid metabolism in liver, that indicate compounds of the present invention can be fast metalized in vivo, produce a short-acting general anesthesia, and be in favor of rapid wake after withdrawal of drug. Thus, the compound of formula (I) and pharmaceutically acceptable salts thereof can be used to prepare central inhibitory drugs that exert sedative, hypnotic and/or anaesthetic effects on humans or animals by venous or extravenous route.

In the following, combing with specific examples of the embodiments shown in FIGURE, above content of the present invention is further illustrated. But it should not be construed that the scope of above subject of the present invention is limited to following examples. Without department from above technical spirits of the present invention, other various alternations or changes made according to the common technical knowledge and the conventional means in the field are all included within the scope of the present invention.

DESCRIPTION OF FIGURE

FIG. 1 is the curve of blood drug level of etomidate and the related pharmacodynamic graph after single administration.

EXAMPLE

Example 1

Chloromethyl chloroformate (CAS: 22128-62-7, 1.29 g) was added to anhydrous dichloromethane (30 mL), to which 0.36 g absolute methanol was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous $Na_2SO_4$. After filtration, the filtrate was evaporated to obtain crude methyl chloromethyl carbonate (1.15 g), that was directly used in the next step of reaction.

216 mg Etomidate acid (CAS: 56649-48-0) was dissolved in 20 mL DMF, to which was successively added methyl chloromethyl carbonate (136 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Colorless oils (234 mg) were obtained by column chromatography, with a yield of 77.0%.

$^1$HNMR (CDCl$_3$, 400 MHz) δ: 1.865 (3H, d, J=4 Hz), 3.84 (3H, s), 5.30 (1H, s), 5.85 (Ha, J=8 Hz), 5.94 (Hb, J=8 Hz), 6.3 (1H, q, J=8 Hz), 7.19~7.37 (5H, m), 7.77 (1H, s), 7.88 (1H, s);

$^{13}$CNMR (CDCl$_3$, 400 MHz) δ: 22.21, 55.36, 55.63, 81.62, 121.14, 126.34, 128.18, 128.93, 139.95, 140.64, 140.81, 154.43, 158.33.

The structure is as follows:

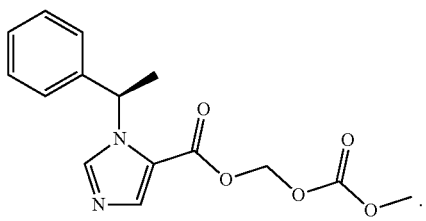 [SMILES: COC(=O)OCOC(=O)c1cncn1[C@H](C)c1ccccc1]

Example 2

Chloromethyl chloroformate (CAS: 22128-62-7, 1.29 g) was added to anhydrous dichloromethane (30 mL), to which 0.48 g absolute ethanol was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous $Na_2SO_4$. After filtration, the filtrate was evaporated to obtain crude ethyl chloromethyl carbonate (1.19 g), that was directly used in the next step of reaction. 216 mg Etomidate acid (CAS: 56649-48-0) was dissolved in 20 mL DMF, to which was successively added ethyl chloromethyl carbonate (165 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Colorless oils (260 mg) were obtained by column chromatography, with a yield of 81.7%.

$^1$HNMR (CDCl$_3$, 400 MHz) δ: 1.33 (3H, t, J=8 Hz), 1.865 (3H, d, J=4 Hz), 4.26 (2H, q, J=8 Hz), 5.85 (Ha, J=8 Hz), 5.94 (Hb, J=8 Hz), 6.31 (1H, q, J=8 Hz), 7.19~7.37 (5H, m), 7.76 (1H, s), 7.88 (1H, s);

$^{13}$CNMR (CDCl$_3$, 400 MHz) δ: 14.13, 22.22, 55.61, 64.87, 81.49, 121.19, 126.35, 128.17, 128.93, 139.90, 140.65, 140.78, 153.87, 158.38.

The structure is as follows:

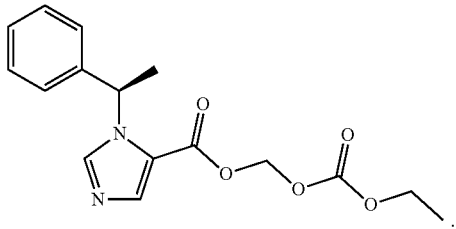 [SMILES: CCOC(=O)OCOC(=O)c1cncn1[C@H](C)c1ccccc1]

Example 3

Chloromethyl chloroformate (CAS: 22128-62-7, 1.29 g) was added to anhydrous dichloromethane (30 mL), to which 0.66 g isopropanol was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous $Na_2SO_4$. After filtration, the filtrate was evaporated to obtain crude isopropyl chloromethyl carbonate (1.28 g), that was directly used in the next step of reaction.

Etomidate acid (216 mg) was dissolved in 20 mL DMF, to which was successively added isopropyl chloromethyl carbonate (155 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Colorless oils (266 mg) were obtained by column chromatography, with a yield of 80.1%.

$^1$HNMR (CDCl$_3$, 400 MHz) δ: 1.33 (6H, d, J=4 Hz), 1.86 (3H, d, J=8 Hz), 4.98 (1H, quint, J=8 Hz), 5.85 (Ha, J=8 Hz), 5.91 (Hb, J=8 Hz), 6.30 (1H, q, J=8 Hz), 7.19~7.36 (5H, m), 7.77 (1H, s), 7.89 (1H, s);

$^{13}$CNMR (CDCl$_3$, 400 MHz) δ: 21.65, 22.20, 55.58, 73.18, 81.40, 121.22, 126.35, 128.16, 128.91, 139.85, 140.66, 140.75, 153.32, 158.40.

The structure is:

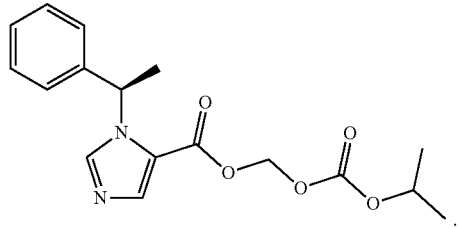 [SMILES: CC(C)OC(=O)OCOC(=O)c1cncn1[C@H](C)c1ccccc1]

Example 4

Chloromethyl chloroformate (CAS: 22128-62-7, 1.29 g) was added to anhydrous dichloromethane (30 mL), to which 0.81 g tert-butanol was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous $Na_2SO_4$. After filtration, the filtrate was evaporated to obtain crude tert-butyl chloromethyl carbonate (1.28 g), that was directly used in the next step of reaction.

Etomidate acid (216 mg) was dissolved in 20 mL DMF, to which was successively added tert-butyl chloromethyl carbonate (182 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Colorless oils (266 mg) were obtained by column chromatography, with a yield of 84.1%.

$^1$HNMR (CDCl$_3$, 400 MHz) δ: 1.50 (9H, s), 1.86 (3H, d, J=8 Hz), 5.82 (Ha, J=4 Hz), 5.88 (Hb, J=4 Hz), 6.32 (1H, q, J=8 Hz), 7.19~7.36 (5H, m), 7.75 (1H, s), 7.87 (1H, s);
$^{13}$CNMR (CDCl$_3$, 400 MHz) δ: 22.18, 27.63, 55.54, 81.08, 83.69, 121.32, 126.36, 128.14, 128.90, 139.75, 140.67, 151.95, 158.49.

The structure is:

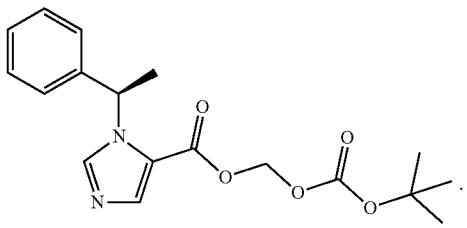 [SMILES: C[C@H](c1ccccc1)n1cncc1C(=O)OCOC(=O)OC(C)(C)C]

Example 5

Chloromethyl chloroformate (CAS: 22128-62-7, 1.29 g) was added to anhydrous dichloromethane (30 mL), to which 0.81 g iso-butanol was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$. After filtration, the filtrate was evaporated to obtain crude iso-butyl chloromethyl carbonate (1.35 g), that was directly used in the next step of reaction.

Etomidate acid (216 mg) was dissolved in 20 mL DMF, to which was successively added iso-butyl chloromethyl carbonate (182 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Colorless oils (275 mg) were obtained by column chromatography, with a yield of 79.5%.

$^1$HNMR (CDCl$_3$, 400 MHz) δ: 0.95 (6H, d, J=8 Hz), 1.86 (3H, d, J=8 Hz), 1.98 (1H, hept, J=8 Hz), 3.98 (2H, d, J=8 Hz), 5.85 (Ha, J=4 Hz), 5.93 (Hb, J=4 Hz), 6.31 (1H, q, J=8 Hz), 7.19~7.36 (5H, m), 7.77 (1H, s), 7.88 (1H, s);
$^{13}$CNMR (CDCl$_3$, 400 MHz) δ: 18.83, 22.20, 27.71, 55.60, 74.80, 81.53, 121.19, 126.34, 128.16, 128.91, 139.90, 140.67, 140.77, 154.04, 158.38.

The structure is:

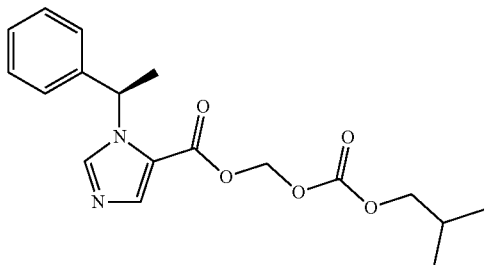

Example 6

Chloromethyl chloroformate (CAS: 22128-62-7, 1.29 g) was added to anhydrous dichloromethane (30 mL), to which 0.81 g sec-butanol was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$. After filtration, the filtrate was evaporated to obtain crude sec-butyl chloromethyl carbonate (1.30 g), that was directly used in the next step of reaction.

Etomidate acid (216 mg) was dissolved in 20 mL DMF, to which was successively added sec-butyl chloromethyl carbonate (182 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Colorless oils (271 mg) were obtained by column chromatography, with a yield of 78.3%.

$^1$HNMR (CDCl$_3$, 400 MHz) δ: 0.95 (6H, d, J=8 Hz), 1.86 (3H, d, J=8 Hz), 1.98 (1H, hept, J=8 Hz), 3.98 (2H, d, J=8 Hz), 5.85 (Ha, J=4 Hz), 5.93 (Hb, J=4 Hz), 6.31 (1H, q, J=8 Hz), 7.19~7.36 (5H, m), 7.77 (1H, s), 7.88 (1H, s).

The structure is:

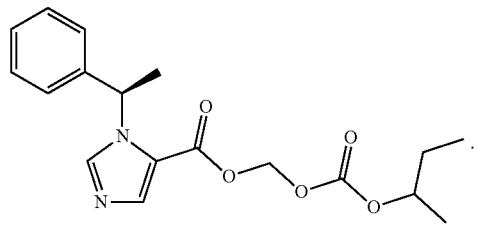 [SMILES: CCC(C)OC(=O)OCOC(=O)c1cncn1[C@H](C)c1ccccc1]

Example 7

1.29 g chloromethyl chloroformate (CAS: 22128-62-7) was added to anhydrous dichloromethane (30 mL), to which cyclobutanol (0.81 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$. After filtration, the filtrate was evaporated to obtain crude cyclobutyl chloromethyl carbonate (1.39 g), that was directly used in the next step of reaction.

Etomidate acid (216 mg) was dissolved in 20 mL DMF, to which was successively added cyclobutyl chloromethyl carbonate (182 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Yellow oils (271 mg) were obtained by column chromatography, with a yield of 78.3%.

$^1$HNMR (CDCl$_3$, 400 MHz) δ: 1.58~1.80 (2H, m), 1.86 (3H, d, J=8 Hz), 2.10~2.22 (2H, m), 2.33~2.41 (2H, m), 4.96 (1H, quint, J=8 Hz), 5.83 (Ha, J=4 Hz), 5.91 (Hb, J=4 Hz), 6.30 (1H, q, J=8 Hz), 7.19~7.37 (5H, m), 7.76 (1H, s), 7.87 (1H, s);

$^{13}$CNMR (CDCl$_3$, 400 MHz) δ: 13.00, 22.21, 29.93, 29.95, 55.62, 72.48, 81.42, 121.18, 126.35, 128.18, 128.93, 139.84, 140.62, 140.76, 152.91, 158.36.

The structure is:

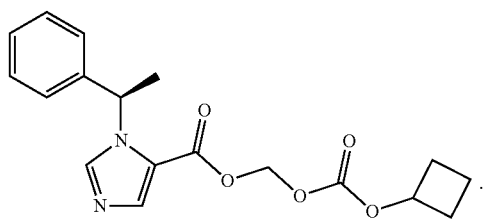 [SMILES: C[C@H](c1ccccc1)n1cncc1C(=O)OCOC(=O)OC1CCC1]

Example 8

1-Chloroethyl chloroformate (CAS: 50893-53-3, 1.43 g) was added to anhydrous dichloromethane (30 mL), to which isopropanol (0.65 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$. After filtration, the filtrate was evaporated to obtain crude 1-chloroethyl chloromethyl carbonate (1.44 g), that was directly used in the next step of reaction. Etomidate acid (216 mg) was dissolved in 20 mL DMF, to which was successively added 1-chloroethyl chloromethyl carbonate (157 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Yellow oils (269 mg) were obtained by column chromatography, with a yield of 76.3%.

$^1$HNMR (CDCl$_3$, 400 MHz) δ: 1.24~1.32 (6H, m), 1.55~1.59 (3H, m), 1.84~1.87 (3H, m), 4.85~4.93 (1H, m), 6.28~6.36 (1H, m), 6.92 (1H, q, J=4 Hz), 7.19~7.33 (5H, m), 7.67 (1H, s), 7.82 (1H, s);

$^{13}$CNMR (CDCl$_3$, 400 MHz) δ: 19.67, 21.59, 21.99, 55.38, 72.74, 90.79, 121.50, 126.55, 128.05, 128.87, 139.28, 140.40, 140.90, 152.41, 157.98.

The structure is:

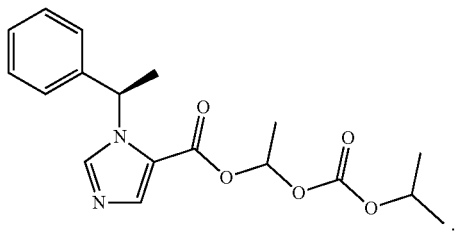

Example 9

Chloromethyl chloroformate (CAS: 22128-62-7, 1.29 g) was added to anhydrous dichloromethane (30 mL), to which hexafluoro-isopropanol (1.68 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$. After filtration, the filtrate was evaporated to obtain crude hexafluoro-isopropyl chloromethyl carbonate (2.02 g), that was directly used in the next step of reaction.

Etomidate acid (216 mg) was dissolved in 20 mL DMF, to which was successively added hexafluoro-isopropyl chloromethyl carbonate (282 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Yellow oils (297 mg) were obtained by column chromatography, with a yield of 67.5%.

$^1$HNMR (CDCl$_3$, 400 MHz) δ: 1.86 (3H, d, J=8 Hz), 5.41~5.51 (2H, m), 6.33~6.45 (1H, m), 7.19~7.37 (5H, m), 7.76 (1H, s), 7.87 (1H, s), 8.76 (1H, m).

The structure is:

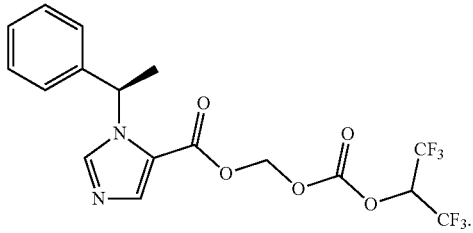 [SMILES: C[C@H](c1ccccc1)n1cncc1C(=O)OCOC(=O)OC(C(F)(F)F)C(F)(F)F]

Example 10

The etomidate derivative (500 mg) according to example 6 was dissolved in absolute methanol (10 mL), to which was drop added 20% hydrogen chloride methanol solution, and pH value of the solution was adjusted to 2~3. The solvent was evaporated under reduced pressure, and the corresponding hydrochlorate (310 mg) was obtained as white powder by column chromatography. The structure is:

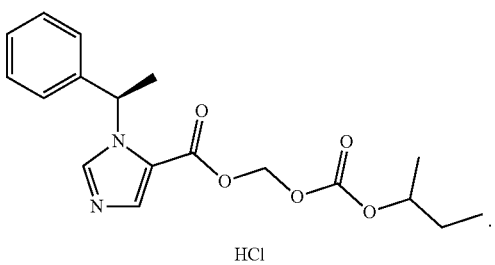 [SMILES: CCC(C)OC(=O)OCOC(=O)c1cncn1[C@H](C)c1ccccc1 ; Cl]

HCl

Example 11

The etomidate derivative (500 mg) according to example 6 was dissolved in absolute methanol (10 mL), to which was added p-toluenesulfonic acid (252 mg). After stirring for 10 min, the solvent was evaporated under reduced pressure, and the transparent semisolid (480 mg) was obtained by column chromatography, i.e. the sulfate of said compound. The structure is:

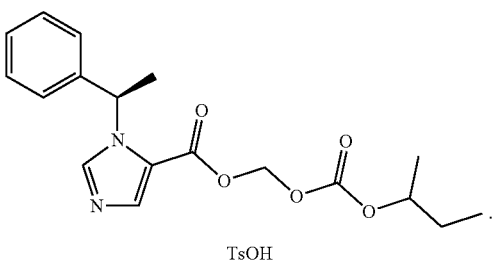

TsOH

Example 12

The etomidate derivative (500 mg) according to example 3 was dissolved in absolute methanol (10 mL), to which was added methanesulfonic acid (145 mg). After stirring for 10 min, the solvent was evaporated under reduced pressure, and the transparent semisolid (307 mg) was obtained by column chromatography, i.e. the methanesulfonate of said compound. The structure is:

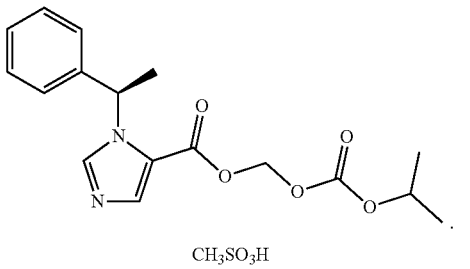

CH$_3$SO$_3$H

Example 13

Chloromethyl chloroformate (CAS: 22128-62-7, 1.29 g) was added to anhydrous dichloromethane (30 mL), to which 1-phenethanol (1.22 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$. After filtration, the filtrate was evaporated to obtain crude 1-phenethyl chloromethyl carbonate (1.99 g), that was directly used in the next step of reaction.

Etomidate acid (216 mg) was dissolved in 20 mL DMF, to which was successively added 1-phenethyl chloromethyl carbonate (235 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Yellow oils (201 mg) were obtained by column chromatography, with a yield of 50.1%.

$^1$HNMR (CDCl$_3$, 400 MHz) δ: 1.60 (3H, d, J=4 Hz), 1.84 (3H, d, J=8 Hz), 5.74~5.93 (3H, m), 6.27 (1H, q, J=8 Hz), 7.18~7.37 (10H, m), 7.75 (1H, s), 7.84 (1H, s);

$^{13}$CNMR (CDCl$_3$, 400 MHz) δ: 22.17, 31.43, 36.47, 55.60, 81.55, 121.19, 126.07, 126.34, 128.15, 128.38, 128.62, 128.91, 139.89, 140.38, 140.65, 140.76, 153.24, 158.34, 162.53.

The structure is:

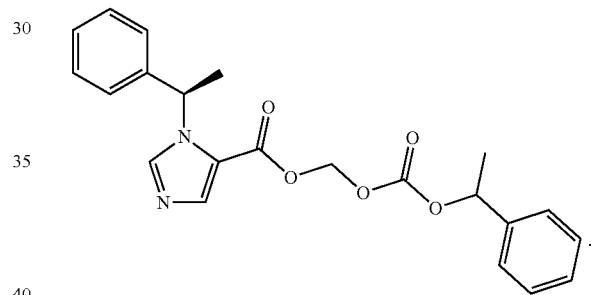

Example 14

Chloromethyl chloroformate (CAS: 22128-62-7, 1.29 g) was added to anhydrous dichloromethane (30 mL), to which p-bromophenol (1.73 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$ overnight. After filtration, the filtrate was evaporated to obtain crude p-bromophenyl chloromethyl carbonate (2.19 g), that was directly used in the next step of reaction.

Etomidate acid (216 mg) was dissolved in 20 mL DMF, to which was successively added p-bromophenyl chloromethyl carbonate (292 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Yellow oils (288 mg) were obtained by column chromatography, with a yield of 64.7%.

¹HNMR (CDCl₃, 400 MHz) δ: 1.85 (3H, d, J=8 Hz), 5.80 (Ha, J=4 Hz), 5.90 (Hb, J=4 Hz), 6.30 (1H, q, J=6 Hz), 7.19~7.36 (9H, m), 7.81 (1H, s), 8.01 (1H, s).

The structure is:

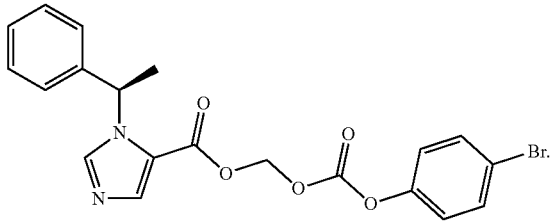 [SMILES: C[C@H](c1ccccc1)n1cncc1C(=O)OCOC(=O)Oc1ccc(Br)cc1]

Example 15

Chloromethyl chloroformate (CAS: 22128-62-7, 1.29 g) was added to anhydrous dichloromethane (30 mL), to which phenol (0.94 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄ overnight. After filtration, the filtrate was evaporated to obtain crude phenyl chloromethyl carbonate (1.79 g), that was directly used in the next step of reaction.

Etomidate acid (216 mg) was dissolved in 20 mL DMF, to which was successively added phenyl chloromethyl carbonate (205 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (221 mg) were obtained by column chromatography, with a yield of 60.4%.

¹HNMR (CDCl₃, 400 MHz) δ: 1.86 (3H, d, J=8 Hz), 5.82 (Ha, J=4 Hz), 5.93 (Hb, J=4 Hz), 6.31 (1H, q, J=6 Hz), 7.17~7.35 (10H, m), 7.80 (1H, s), 7.99 (1H, s).

The structure is:

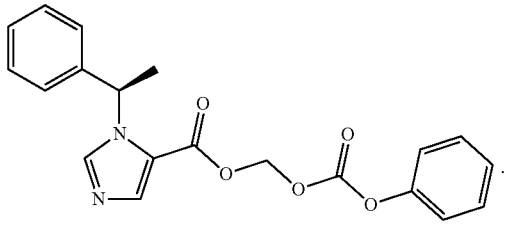 [SMILES: C[C@H](c1ccccc1)n1cncc1C(=O)OCOC(=O)Oc1ccccc1]

Example 16

Chloromethyl chloroformate (CAS: 22128-62-7, 1.29 g) was added to anhydrous dichloromethane (30 mL), to which R-(−)-2-butanol (0.74 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄ overnight. After filtration, the filtrate was evaporated to obtain crude R-(−)-2-butyl chloromethyl carbonate (1.79 g), that was directly used in the next step of reaction.

Etomidate acid (216 mg) was dissolved in 20 mL DMF, to which was successively added R-(−)-2-butyl chloromethyl carbonate (172 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (301 mg) were obtained by column chromatography, with a yield of 87.0%.

¹HNMR (DMSO-D₆, 400 MHz) δ: 0.85 (6H, m), 1.42 (3H, m), 1.58 (2H), 1.85 (3H, d, J=6 Hz), 4.65~4.80 (1H, m), 5.83 (1H, m), 6.21 (1H, m), 7.19~7.35 (5H, m), 7.75 (1H, s), 8.45 (1H, s).

The structure is:

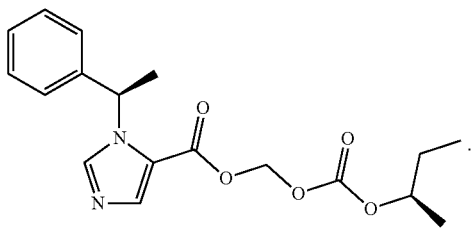 [SMILES: CC[C@@H](C)OC(=O)OCOC(=O)c1cncn1[C@H](C)c1ccccc1]

Example 17

Chloromethyl chloroformate (CAS: 22128-62-7, 1.29 g) was added to anhydrous dichloromethane (30 mL), to which S-(+)-2-butanol (0.74 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄ overnight. After filtration, the filtrate was evaporated to obtain crude S-2-butyl chloromethyl carbonate (1.79 g), that was directly used in the next step of reaction.

Etomidate acid (216 mg) was dissolved in 20 mL DMF, to which was successively added (S)-2-butyl chloromethyl carbonate (172 mg) and potassium carbonate (275 mg), and the mixture was stirred at room temperature for 3 hours, then subjected to TLC detection. The starting material was almost completely reacted. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (288 mg) were obtained by column chromatography, with a yield of 83.2%.

¹HNMR (DMSO-D₆, 400 MHz) δ: 0.82 (6H, m), 1.41 (3H, m), 1.54 (2H), 1.83 (3H, d, J=6 Hz), 4.61~4.81 (1H, m), 5.82 (1H, m), 6.11 (1H, m), 7.09~7.25 (5H, m), 7.73 (1H, s), 8.41 (1H, s).

The structure is:

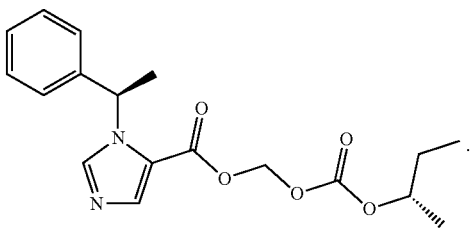 [SMILES: CC[C@H](C)OC(=O)OCOC(=O)c1cncn1[C@H](C)c1ccccc1]

Example 18

Iso-chlorobutyl chloroformate (CAS: 22128-62-7, 1.71 g) was added to anhydrous dichloromethane (30 mL), to which absolute ethanol (0.50 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous $Na_2SO_4$ overnight. After filtration, the filtrate was evaporated to obtain crude iso-chlorobutyl chloromethyl carbonate (1.3 g), that was directly used in the next step of reaction.

Etomidate acid (216 mg) was dissolved in 20 mL absolute ethanol, to which was successively added iso-chlorobutyl chloromethyl carbonate (200 mg) and potassium carbonate (275 mg), and the mixture was stirred at room temperature for 10 hours. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Pale yellow oils (107 mg) were obtained by column chromatography, with a yield of 29.7%.

$^1$HNMR (CDCl$_3$, 400 MHz) δ: 0.97~1.05 (6H, m), 1.30~1.34 (3H, m), 1.82~1.91 (3H, m), 2.87~2.98 (1H, m), 6.35 (1H, d, J=6 Hz), 6.77 (1H, q, J=4 Hz), 7.21~7.35 (5H, m), 7.64~7.80 (2H, m).

The structure is:

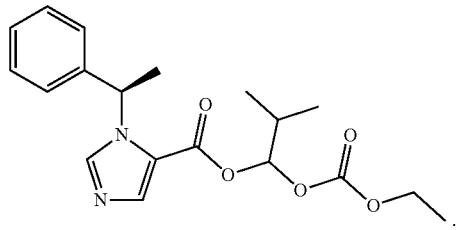 [SMILES: CCOC(=O)OC(OC(=O)c1cncn1[C@H](C)c1ccccc1)C(C)C]

Example 19

Preparation of product in example 1 using acetonitrile as solvent: etomidate acid (216 mg, CAS: 56649-48-0) was dissolved in 20 mL acetonitrile, to which was successively added methyl chloromethyl carbonate (136 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Said product in Example 1 (182 mg) was obtained as colorless oils by column chromatography, with a yield of 59.9%.

Example 20

Preparation of product in example 1 using dimethylsulfoxide (DMSO) as solvent: etomidate acid (216 mg, CAS: 56649-48-0) was dissolved in 20 mL DMSO, to which was successively added methyl chloromethyl carbonate (136 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Said product in Example 1 (194 mg) was obtained as colorless oils by column chromatography, with a yield of 63.9%.

Example 21

Chloromethyl chloroformate (CAS: 22128-62-7, 1.29 g) was added to anhydrous dichloromethane (30 mL), to which octadecanol (2.70 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous $Na_2SO_4$ overnight. After filtration, the filtrate was evaporated to obtain crude octadecanyl chloromethyl carbonate (2.79 g), that was directly used in the next step of reaction.

Etomidate acid (216 mg) was dissolved in 20 mL DMF, to which was successively added octadecanyl chloromethyl carbonate (350 mg) and potassium carbonate (275 mg), and the mixture was stirred at room temperature for 7 hours. After the reaction solution was filtered, the reaction was poured to 150 mL water, and extracted with 100 mL dichloromethane. The organic layer was separated and dried over anhydrous $Na_2SO_4$ overnight. On the second day, the reaction was filtered to obtain the filtrate, that was concentrated under reduced pressure to provide yellow oils. Pale yellow oils (401 mg) were obtained by column chromatography, with a yield of 75.7%.

$^1$HNMR (CDCl$_3$, 400 MHz) δ: 0.86~1.70 (37H, m), 1.86 (3H, d, J=8 Hz), 5.53~5.93 (2H, m), 6.28~6.39 (1H, m), 7.18~7.35 (5H, m), 7.73~7.88 (2H, m).

The structure is:

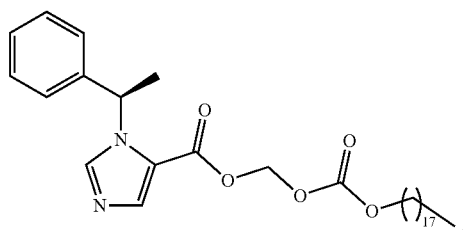

Example 22

Chloromethyl carbonate (CAS: 22128-62-7, 1.29 g) was added to anhydrous dichloromethane (30 mL), to which nitroethanol (1 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$ overnight. After filtration, the filtrate was evaporated to obtain crude nitroethyl chloromethyl carbonate (1.49 g), that was directly used in the next step of reaction.

Etomidate acid (CAS: 56649-48-0, 216 mg) was dissolved in 20 mL DMF, to which was successively added nitroethyl chloromethyl carbonate (195 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Pale yellow oils (280 mg) were obtained by column chromatography, with a yield of 77.1%.

$^1$HNMR (CDCl$_3$, 400 MHz) δ: 1.86 (3H, d, J=4 Hz), 4.65~4.79 (4H, m), 5.85~5.94 (2H, m), 6.32 (1H, q, J=8 Hz), 7.17~7.36 (5H, m), 7.77 (1H, s), 7.87 (1H, s).

The structure is:

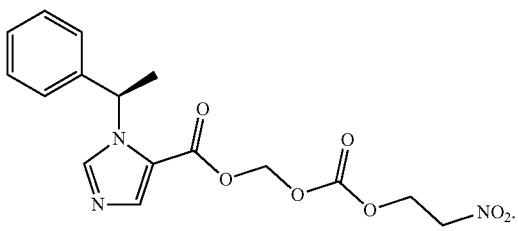 [SMILES: C[C@H](c1ccccc1)n1cncc1C(=O)OCOC(=O)OCC[N+](=O)[O-]]

Example 23

Chloromethyl chloroformate (CAS: 22128-62-7, 1.29 g) was added to anhydrous dichloromethane (30 mL), to which trichloroethanol (1.5 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$ overnight. After filtration, the filtrate was evaporated to obtain crude trichloroethyl chloromethyl carbonate (2.09 g), that was directly used in the next step of reaction.

Etomidate acid (CAS: 56649-48-0, 216 mg) was dissolved in 20 mL DMF, to which was successively added trichloroethyl chloromethyl carbonate (255 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Pale yellow oils (211 mg) were obtained by column chromatography, with a yield of 50.0%.

$^1$HNMR (CDCl$_3$, 400 MHz) δ: 1.86~1.89 (3H, m), 4.19~4.27 (2H, d, J=32 Hz), 5.50~5.61 (2H, m), 6.29~6.36 (1H, m), 7.16~7.34 (5H, m), 7.77~7.87 (2H, m).

The structure is:

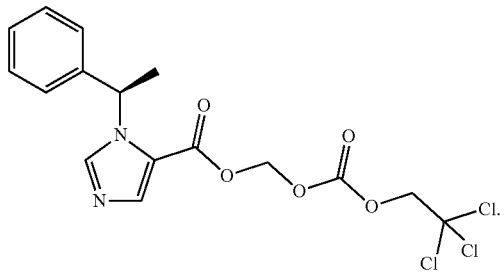 [SMILES: C[C@H](c1ccccc1)n1cncc1C(=O)OCOC(=O)OCC(Cl)(Cl)Cl]

Example 24

1-Chloroethyl chloroformate (CAS: 50893-53-3, 1.43 g) was added to anhydrous dichloromethane (30 mL), to which methanol (0.60 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$. After filtration, the filtrate was evaporated to obtain crude 1-chloroethyl methyl carbonate (1.01 g), that was directly used in the next step of reaction.

Etomidate acid (216 mg) was dissolved in 5 mL H$_2$O and 20 mL acetonitrile, to which was successively added 1-chloroethyl methyl carbonate (160 mg) and potassium carbonate (275 mg), and the mixture was stirred at the temperature of −10° C. for 20 hours. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Pale yellow oils (189 mg) were obtained by column chromatography, with a yield of 59.4%.

$^1$HNMR (CDCl$_3$, 400 MHz) δ: 1.54~1.58 (3H, m), 1.82~1.85 (3H, m), 3.81 (3H, s), 6.23~6.35 (1H, m), 6.82 (1H, q, J=4 Hz), 7.18~7.32 (5H, m), 7.66 (1H, s), 7.81 (1H, s).

The structure is:

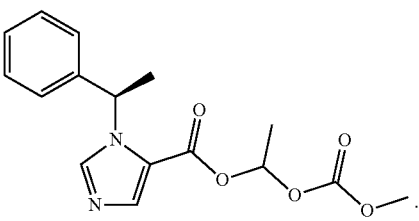 [SMILES: COC(=O)OC(C)OC(=O)c1cncn1[C@H](C)c1ccccc1]

Example 25

1-Chloroethyl chloroformate (CAS: 50893-53-3, 1.43 g) was added to anhydrous dichloromethane (30 mL), to which absolute ethanol (0.65 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude 1-chloroethyl ethyl carbonate (1.21 g), that was directly used in the next step of reaction.

Etomidate acid (216 mg) was dissolved in 5 mL H₂O and 20 mL acetonitrile, to which was successively added 1-chloroethyl ethyl carbonate (160 mg) and potassium carbonate (275 mg), and the mixture was stirred at the temperature of −10° C. for 20 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (195 mg) were obtained by column chromatography, with a yield of 58.7%.

¹HNMR (CDCl₃, 400 MHz) δ: 1.34~1.38 (3H, m), 1.51~1.55 (3H, m), 1.82~1.85 (3H, m), 4.25~4.30 (2H, m), 6.21~6.34 (1H, m), 6.79 (1H, q, J=4 Hz), 7.15~7.31 (5H, m), 7.61 (1H, s), 7.79 (1H, s).

The structure is:

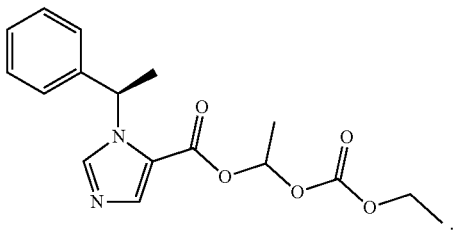 [SMILES: CCOC(=O)OC(C)OC(=O)c1cncn1[C@H](C)c1ccccc1]

Example 26

1-Chloropropyl chloroformate (CAS: 92600-20-9, 1.56 g) was added to anhydrous dichloromethane (30 mL), to which methanol (0.55 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude 1-chloropropyl methyl carbonate (1.31 g), that was directly used in the next step of reaction.

Etomidate acid (216 mg) was dissolved in 5 mL H₂O and 20 mL acetonitrile, to which was successively added 1-chloropropyl methyl carbonate (170 mg) and potassium carbonate (275 mg), and the mixture was stirred at the temperature of −10° C. for 20 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (115 mg) were obtained by column chromatography, with a yield of 34.6%.

¹HNMR (CDCl₃, 400 MHz) δ: 0.89~1.00 (3H, m), 3.75 (3H, s), 1.81~1.92 (5H, m), 6.26~6.31 (1H, m), 6.75 (1H, q, J=4 Hz), 7.16~7.30 (5H, m), 7.64~7.82 (2H, m).

The structure is:

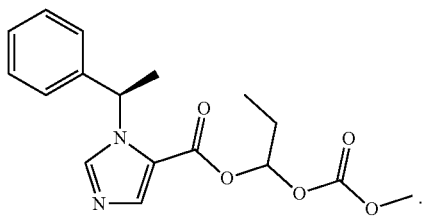 [SMILES: CCC(OC(=O)OC)OC(=O)c1cncn1[C@H](C)c1ccccc1]

Example 27

1-Chloropropyl chloroformate (CAS: 92600-20-9, 1.56 g) was added to anhydrous dichloromethane (30 mL), to which absolute ethanol (0.60 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude 1-chloropropyl ethyl carbonate (1.35 g), that was directly used in the next step of reaction.

Etomidate acid (216 mg) was dissolved in 5 mL H₂O and 20 mL acetonitrile, to which was successively added 1-chloropropyl ethyl carbonate (180 mg) and potassium carbonate (275 mg), and the mixture was stirred at the temperature of −10° C. for 20 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (121 mg) were obtained by column chromatography, with a yield of 35.0%.

¹HNMR (CDCl₃, 400 MHz) δ: 0.93~1.01 (3H, m), 1.25~1.30 (3H, m), 1.81~1.91 (5H, m), 4.19~4.43 (2H, m), 6.28~6.34 (1H, m), 6.77 (1H, q, J=4 Hz), 7.17~7.31 (5H, m), 7.65~7.80 (2H, m).

The structure is:

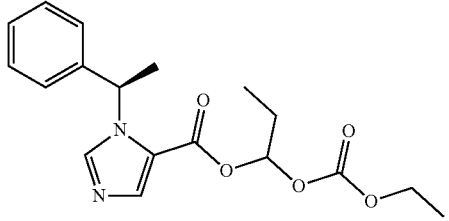

Example 28

1-Chloropropyl chloroformate (CAS: 92600-20-9, 1.56 g) was added to anhydrous dichloromethane (30 mL), to which isopropanol (0.65 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude 1-chloropropyl isopropyl carbonate (1.47 g), that was directly used in the next step of reaction.

Etomidate acid (216 mg) was dissolved in 5 mL H₂O and 20 mL acetonitrile, to which was successively added 1-chloropropyl isopropyl carbonate (180 mg) and potassium carbonate (275 mg), and the mixture was stirred at the temperature of −10° C. for 52 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (120 mg) were obtained by column chromatography, with a yield of 30.0%.

¹HNMR (CDCl₃, 400 MHz) δ: 0.95~1.03 (3H, m), 1.28~1.32 (6H, m), 1.84~1.93 (5H, m), 4.85~4.93 (1H, m), 6.30~6.37 (1H, m), 6.79 (1H, q, J=4 Hz), 7.20~7.34 (5H, m), 7.66~7.82 (2H, m).

The structure is:

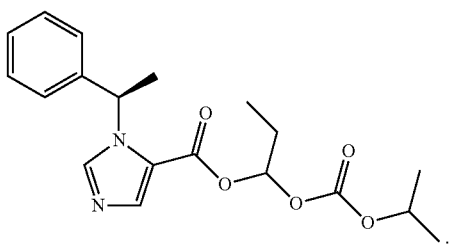 [SMILES: CCC(OC(=O)OC(C)C)OC(=O)c1cncn1[C@H](C)c1ccccc1]

Example 29

Chloroisobutyl chloroformate (CAS: 92600-11-8, 1.71 g) was added to anhydrous dichloromethane (30 mL), to which methanol (0.50 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude methyl chloroisobutyl carbonate (1.21 g), that was directly used in the next step of reaction.

Etomidate acid (216 mg) was dissolved in 5 mL H₂O and 20 mL acetonitrile, to which was successively added methyl chloroisobutyl carbonate (180 mg) and potassium carbonate (275 mg), and the mixture was stirred at the temperature of −10° C. for 60 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (117 mg) were obtained by column chromatography, with a yield of 33.8%.

¹HNMR (CDCl₃, 400 MHz) δ: 0.98~1.07 (6H, m), 1.81~1.93 (3H, m), 3.13 (3H, s), 6.33 (1H, d, J=6 Hz), 6.77 (1H, q, J=4 Hz), 7.21~7.35 (5H, m), 7.64~7.80 (2H, m).

The structure is:

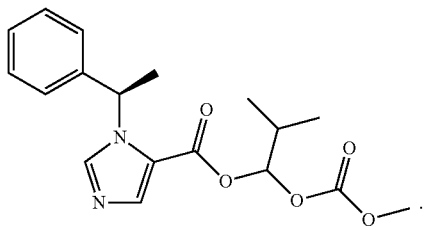 [SMILES: COC(=O)OC(OC(=O)c1cncn1[C@H](C)c1ccccc1)C(C)C]

Example 30

Chloroisobutyl chloroformate (CAS: 92600-11-8, 1.71 g) was added to anhydrous dichloromethane (30 mL), to which isopropyl (0.65 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude isopropyl chloroisobutyl carbonate (1.21 g), that was directly used in the next step of reaction.

Etomidate acid (216 mg) was dissolved in 5 mL H₂O and 20 mL acetonitrile, to which was successively added isopropyl chloroisobutyl carbonate (230 mg) and potassium carbonate (275 mg), and the mixture was stirred at the temperature of −10° C. for 60 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (127 mg) were obtained by column chromatography, with a yield of 34.0%.

¹HNMR (CDCl₃, 400 MHz) δ: 0.98~1.07 (6H, m), 1.81~1.89 (6H, m), 2.79 (1H, m), 4.87~4.92 (1H, m), 6.33 (1H, d, J=6 Hz), 6.77 (1H, q, J=4 Hz), 7.21~7.35 (5H, m), 7.64~7.80 (2H, m).

The structure is:

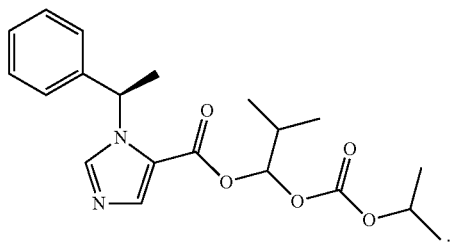 [SMILES: CC(C)OC(=O)OC(OC(=O)c1cncn1[C@H](C)c1ccccc1)C(C)C]

Example 31

2-allyl chloroformate (CAS: 57933-83-2, 1.2 g) was added to anhydrous dichloromethane (30 mL), to which methanol (0.45 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude methyl 2-allyl carbonate (1.21 g), to which was added the solution of 4 M HCl in dioxane (20 mL). The mixture was stirred at room temperature for 10 h, and then the solvent was evaporated under reduced pressure, to obtain methyl 1,1-dimethylchloromethyl carbonate (1.21 g).

Etomidate acid (216 mg) was dissolved in 5 mL H₂O and 20 mL acetonitrile, to which was successively added methyl 1,1-dimethylchloromethyl carbonate (160 mg) and potassium carbonate (275 mg), and the mixture was stirred at the temperature of −10° C. for 60 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (87 mg) were obtained by column chromatography, with a yield of 26.2%.

¹HNMR (CDCl₃, 400 MHz) δ: 1.67 (3H, s), 1.72 (3H, s), 1.82~1.90 (3H, m), 3.49 (3H, s), 6.75 (1H, q, J=4 Hz), 7.20~7.33 (5H, m), 7.64 (1H, s), 7.80 (1H, s).

The structure is:

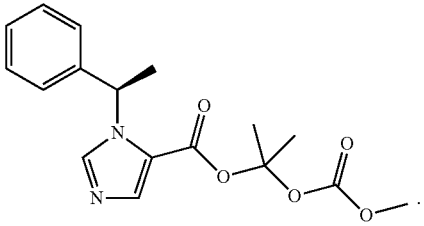 [SMILES: COC(=O)OC(C)(C)OC(=O)c1cncn1[C@H](C)c1ccccc1]

Example 32

2-allyl chloroformate (CAS: 57933-83-2, 1.2 g) was added to anhydrous dichloromethane (30 mL), to which absolute alcohol (0.55 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude ethyl 2-allyl carbonate (0.91 g), to which was added the solution of 4 M HCl in dioxane (20 mL).

The mixture was stirred at room temperature for 10 h, and then the solvent was evaporated under reduced pressure, to obtain ethyl 1,1-dimethylchloromethyl carbonate (1.16 g).

Etomidate acid (216 mg) was dissolved in 5 mL H₂O and 20 mL acetonitrile, to which was successively added ethyl 1,1-dimethylchloromethyl carbonate (175 mg) and potassium carbonate (275 mg), and the mixture was stirred at the temperature of −10° C. for 60 hours. After the reaction solution was filtered, the reaction was poured to 150 mL water, and extracted with 100 mL dichloromethane.

The organic layer was separated and dried over anhydrous Na₂SO₄ overnight. On the second day, the reaction was filtered to obtain the filtrate, that was concentrated under reduced pressure to provide yellow oils. Pale yellow oils (97 mg) were obtained by column chromatography, with a yield of 28.0%.

¹HNMR (CDCl₃, 400 MHz) δ: 1.28~1.33 (3H, m), 1.65 (3H, s), 1.71 (3H, s), 1.82~1.90 (3H, m), 4.28~4.33 (2H, m), 6.73 (1H, q, J=4 Hz), 7.23~7.35 (5H, m), 7.68 (1H, s), 7.82 (1H, s).

The structure is:

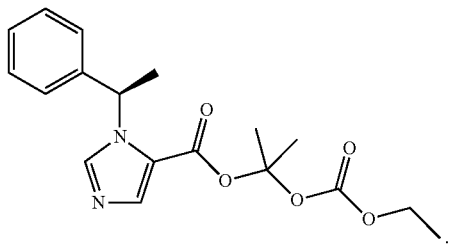 [SMILES: CCOC(=O)OC(C)(C)OC(=O)c1cncn1[C@H](C)c1ccccc1]

Example 33

2-Allyl chloroformate (CAS: 57933-83-2, 1.2 g) was added to anhydrous dichloromethane (30 mL), to which isopropanol (0.65 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na₂SO₄. After filtration, the filtrate was evaporated to obtain crude isopropyl 2-allyl carbonate (0.99 g), to which was added the solution of 4 M HCl in dioxane (20 mL). The mixture was stirred at room temperature for 10 h, and then the solvent was evaporated under reduced pressure, to obtain isopropyl 1,1-dimethylchloromethyl carbonate (1.23 g).

Etomidate acid (216 mg) was dissolved in 5 mL H₂O and 20 mL acetonitrile, to which was successively added isopropyl 1,1-dimethylchloromethyl carbonate (200 mg) and potassium carbonate (275 mg), and the mixture was stirred at the temperature of −10° C. for 60 hours. After the reaction solution was filtered, the reaction was poured to 150 mL water, and extracted with 100 mL dichloromethane. The organic layer was separated and dried over anhydrous Na₂SO₄ overnight. On the second day, the reaction was filtered to obtain the filtrate, that was concentrated under reduced pressure to provide yellow oils. Pale yellow oils (112 mg) were obtained by column chromatography, with a yield of 31.1%.

¹HNMR (CDCl₃, 400 MHz) δ: 1.25~1.30 (6H, m), 1.68 (3H, s), 1.75 (3H, s), 1.85~1.91 (3H, m), 4.84~4.91 (1H, m), 6.71 (1H, q, J=4 Hz), 7.26~7.38 (5H, m), 7.69 (1H, s), 7.92 (1H, s).

The structure is:

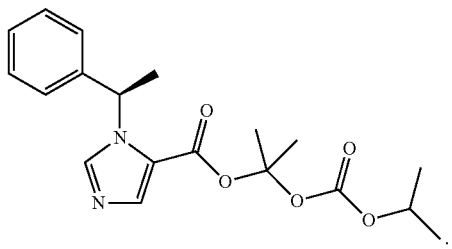 [SMILES: CC(C)OC(=O)OC(C)(C)OC(=O)c1cncn1[C@H](C)c1ccccc1]

Example 34

1-Ethoxylcyclopropanol (CAS: 13837-45-1, 204 mg) and etomidate acid (432 mg) were dissolved in dichloromethane (30 mL), to which was added catalytic amount of 4-dimethylaminopyridine (DMAP), and then the solution of dicyclohexylcarbodiimide (DCC, 440 mg) in dichloromethane (10 mL) was slowly drop added. After addition, the mixture was stirred at room temperature for 2 hours, filtered, and the solvent was evaporated to obtain the crude product, that was directly dissolved in the solution of 60% methanol in water. pH value of the solution was adjusted to 2 by drop adding hydrochloric acid, and the mixture was stirred at room temperature for 30 min. Most of methanol was removed under reduced pressure, and the solution was extracted with ethyl acetate. The organic layer was separated and dried over anhydrous $Na_2SO_4$ overnight. On the second day, the reaction was filtered to obtain the filtrate, that was evaporated under reduced pressure to provide 1-hydroxycyclopropyl etomidate (306 mg), with a yield of 56.3%.

1-Hydroxycyclopropyl etomidate (273 mg) and methyl chloroformate (CAS: 79-22-1, 100 mg) were dissolved in dichloromethane (30 mL), to which was added pyridine (320 mg) on ice bath, and after removal of ice bath, the mixture was stirred at room temperature for 3 h. The organic layer was washed with water once, separated, and dried over anhydrous $Na_2SO_4$ overnight. On the second day, the reaction was filtered to obtain the filtrate, that was evaporated under reduced pressure to provide the target compound (306 mg) by column chromatography, with a yield of 71.5%.

$^1$HNMR (CDCl$_3$, 400 MHz) δ: 1.12~1.27 (4H, m), 1.85~1.91 (3H, m), 3.24 (3H, s), 6.70 (1H, q, J=4 Hz), 7.22~7.34 (5H, m), 7.66 (1H, s), 7.91 (1H, s).

The structure is:

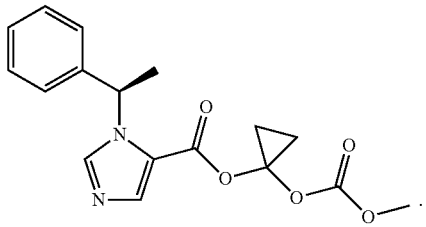 [SMILES: COC(=O)OC1(OC(=O)c2cncn2[C@H](C)c2ccccc2)CC1]

Example 35

According the method of example 34, 1-hydroxycyclopropyl etomidate was prepared. 1-Hydroxycyclopropyl etomidate (273 mg) and ethyl chloroformate (CAS: 541-41-3, 120 mg) were dissolved in dichloromethane (30 mL), to which was added pyridine (320 mg) on ice bath, and after removal of ice bath, the mixture was stirred at room temperature for 3 h. The organic layer was washed with water once, separated, and dried over anhydrous $Na_2SO_4$ overnight. On the second day, the reaction was filtered to obtain the filtrate, that was evaporated under reduced pressure to provide the target compound (216 mg) by column chromatography, with a yield of 62.8%.

$^1$HNMR (CDCl$_3$, 400 MHz) δ: 1.13~1.25 (7H, m), 1.84~1.92 (3H, m), 4.24~4.30 (2H, m), 6.72 (1H, q, J=4 Hz), 7.23~7.35 (5H, m), 7.67 (1H, s), 7.90 (1H, s).

The structure is:

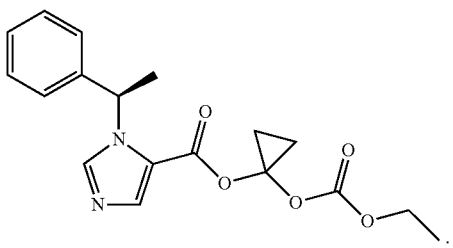 [SMILES: CCOC(=O)OC1(OC(=O)c2cncn2[C@H](C)c2ccccc2)CC1]

Example 36

According the method of example 34, 1-hydroxycyclopropyl etomidate was prepared. 1-Hydroxycyclopropyl etomidate (273 mg) and isopropyl chloroformate (CAS: 541-41-3, 140 mg) were dissolved in dichloromethane (30 mL), to which was added pyridine (320 mg) on ice bath, and after removal of ice bath, the mixture was stirred at room temperature for 3 h. The organic layer was washed with water once, separated, and dried over anhydrous $Na_2SO_4$ overnight. On the second day, the reaction was filtered to obtain the filtrate, that was evaporated under reduced pressure to provide the target compound (251 mg) by column chromatography, with a yield of 70.1%.

$^1$HNMR (CDCl$_3$, 400 MHz) δ: 1.12~1.33 (10H, m), 1.83~1.90 (3H, m), 4.64~4.70 (1H, m), 6.72 (1H, q, J=4 Hz), 7.21~7.32 (5H, m), 7.68 (1H, s), 7.94 (1H, s).

The structure is:

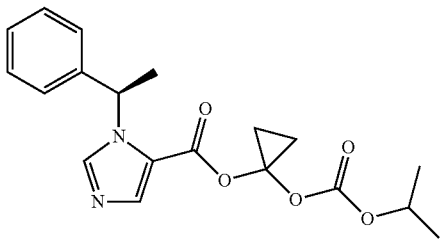

Example 37

1-Ethoxylcyclobutanol (CAS: 102309-15-9, 232 mg) and etomidate acid (432 mg) were dissolved in dichloromethane (30 mL), to which was added catalytic amount of 4-dimethylaminopyridine (DMAP), and then the solution of dicyclohexylcarbodiimide (DCC, 440 mg) in dichloromethane (10 mL) was slowly drop added. After addition, the mixture was stirred at room temperature for 2 hours, filtered, and the solvent was evaporated to obtain the crude product, that was directly dissolved in the solution of 60% methanol in water. pH value of the solution was adjusted to 2 by drop adding hydrochloric acid, and the mixture was stirred at room temperature for 30 min. Most of methanol was removed under reduced pressure, and the solution was extracted with ethyl acetate. The organic layer was separated and dried over anhydrous $Na_2SO_4$ overnight. On the second day, the reaction was filtered to obtain the filtrate, that was evaporated under reduced pressure to provide 1-hydroxycyclobutyl etomidate (298 mg), with a yield of 52.1%.

1-Hydroxycyclobutyl etomidate (273 mg) and methyl chloroformate (CAS: 79-22-1, 100 mg) were dissolved in dichloromethane (30 mL), to which was added pyridine (320 mg) on ice bath, and after removal of ice bath, the mixture was stirred at room temperature for 3 h. The organic layer was washed with water once, separated, and dried over anhydrous Na$_2$SO$_4$ overnight. On the second day, the reaction was filtered to obtain the filtrate, that was evaporated under reduced pressure to provide the target compound (225 mg) by column chromatography, with a yield of 65.4%.

$^1$HNMR (CDCl$_3$, 400 MHz) δ: 1.84~1.88 (3H, m), 2.16~2.34 (6H, m), 3.14 (3H, s), 6.70 (1H, q, J=4 Hz), 7.25~7.38 (5H, m), 7.69 (1H, s), 7.93 (1H, s).

The structure is:

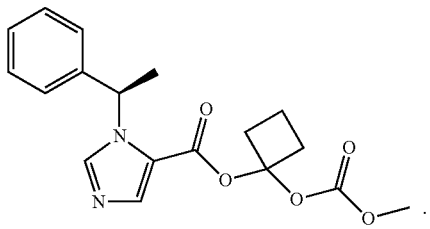 [SMILES: COC(=O)OC1(OC(=O)c2cncn2[C@H](C)c2ccccc2)CCC1]

Example 38

Chloromethyl chloroformate (CAS: 22128-62-7, 1.29 g) was added to anhydrous dichloromethane (30 mL), to which difluoroethanol (0.9 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$ overnight. After filtration, the filtrate was evaporated to obtain crude ethyl chloromethyl carbonate (1.37 g), that was directly used in the next step of reaction.

Etomidate acid (CAS: 56649-48-0, 216 mg) was dissolved in 20 mL DMF, to which was successively added diethyl chloromethyl carbonate (180 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Pale yellow oils (215 mg) were obtained by column chromatography, with a yield of 60.7%.

$^1$HNMR (CDCl$_3$, 400 MHz) δ: 1.85 (3H, d, J=8 Hz), 4.50~4.56 (2H, m), 5.41~5.51 (2H, m), 5.77~5.81 (1H, m), 6.28~6.39 (1H, m), 7.18~7.35 (5H, m), 7.69 (1H, s), 7.91 (1H, s).

The structure is:

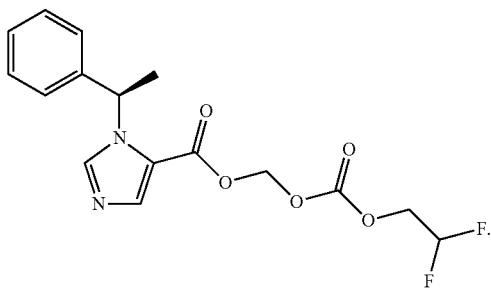 [SMILES: C[C@H](c1ccccc1)n1cncc1C(=O)OCOC(=O)OCC(F)F]

Example 39

Chloromethyl chloroformate (CAS: 22128-62-7, 1.29 g) was added to anhydrous dichloromethane (30 mL), to which 2-methyl-3-buten-2-ol (CAS: 115-18-4, 0.95 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$ overnight. After filtration, the filtrate was evaporated to obtain crude 2-methyl-3-buten-2-yl chloromethyl carbonate (1.67 g), that was directly used in the next step of reaction.

Etomidate acid (CAS: 56649-48-0, 216 mg) was dissolved in 20 mL DMF, to which was successively added 2-methyl-3-buten-2-yl chloromethyl carbonate (180 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Colorless oils (215 mg) were obtained by column chromatography, with a yield of 85.2%.

$^1$HNMR (CDCl$_3$, 400 MHz) δ: 1.21~1.24 (6H, d, J=12 Hz), 1.83 (3H, d, J=8 Hz), 5.28~5.31 (2H, m), 5.41~5.51 (2H, m), 5.91 (1H, m), 6.24~6.35 (1H, m), 7.14~7.31 (5H, m), 7.71 (1H, s), 7.81 (1H, s).

The structure is:

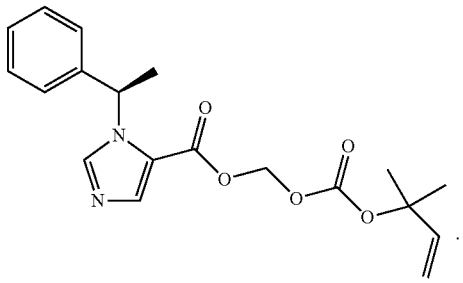 [SMILES: C=CC(C)(C)OC(=O)OCOC(=O)c1cncn1[C@H](C)c1ccccc1]

Example 40

Chloromethyl chloroformate (CAS: 22128-62-7, 1.29 g) was added to anhydrous dichloromethane (30 mL), to which 3-methyl-2-buten-1-ol (CAS: 556-82-1, 0.95 g) was added, and under cold water cooling, 1.6 g pyridine was drop added, and the mixture was stirred for 2 hours. Dichloromethane (50 mL) was added, and the organic layer was washed with 2N hydrochloric acid twice, then washed with water once. The organic layer was separated and dried over anhydrous Na$_2$SO$_4$ overnight. After filtration, the filtrate was evaporated to obtain crude 3-methyl-2-buten-1-yl chloromethyl carbonate (1.62 g), that was directly used in the next step of reaction.

Etomidate acid (CAS: 56649-48-0, 216 mg) was dissolved in 20 mL DMF, to which was successively added 3-methyl-2-buten-1-yl chloromethyl carbonate (180 mg) and potassium carbonate (275 mg), and the mixture was stirred at room temperature for 3 hours. After the reaction solution was filtered, the reaction was poured to 150 mL water, and extracted with 100 mL dichloromethane. The organic layer was separated and dried over anhydrous Na$_2$SO$_4$ overnight. On the second day, the reaction was filtered to obtain the filtrate, that was concentrated under reduced pressure to provide yellow oils. Colorless oils (301 mg) were obtained by column chromatography, with a yield of 84.1%.

$^1$HNMR (CDCl$_3$, 400 MHz) δ: 1.71 (3H, s), 1.82 (3H, s), 1.85 (3H, d, J=8 Hz), 4.78 (2H, d, J=8 Hz), 5.41~5.51 (1H, m), 5.61~5.81 (2H, s), 6.24~6.35 (1H, m), 7.14~7.31 (5H, m), 7.71 (1H, s), 7.81 (1H, s).

The structure is:

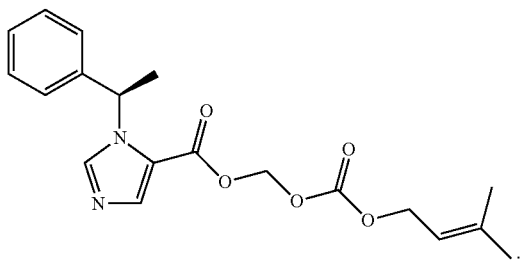 [SMILES: CC(C)=CCOC(=O)OCOC(=O)c1cncn1[C@H](C)c1ccccc1]

Example 41

150 male SD rats weighing 250~300 g were randomly divided into 15 groups, 10 rats for one group. Compounds of some examples above, as well as the control drug etomidate, MOC-ET, and CPMM were dissolved in DMSO, and 2ED$_{50}$ of each drug in rats was used as the administration dose, while the blank control group received the same volume of DMSO. Drugs were injected to rats via caudal vein, and the injection time was 15 seconds. The abolition of righting reflex for 30 s or above was used as the indicator producing anaesthetic effect. The results are shown in Table 1.

TABLE 1

Results of inducing anaesthetic effect of compounds of part examples and control drugs.

| Drugs | Dose (2ED$_{50}$) mg/kg | Time of keeping anaesthesia[1] (min) | Time of complete recovery[2] (min) | Incidence rate (%) of muscle tremor |
| --- | --- | --- | --- | --- |
| DMSO | — | — | — | — |
| Etomidate | 2.0 | 6.3 ± 2.8 | 7.2 ± 1.7 | 40% |
| CPMM | 4.0 | 2.5 ± 1.3 | 2.3 ± 2.1 | 80% |
| Example 1 | 13.8 | 1.5 ± 0.6 | 1.4 ± 0.5 | 0 |
| Example 2 | 13.2 | 1 ± 0.5 | 2.5 ± 0.4 | 0 |
| Example 3 | 4.6 | 2.1 ± 0.3 | 1.3 ± 0.5 | 0 |
| Example 4 | 5.0 | 8.3 ± 1.4 | 6.1 ± 1.6 | 0 |
| Example 5 | 14.0 | 3 ± 1.1 | 3.3 ± 2.1 | 10% |
| Example 6 | 6.4 | 2.4 ± 0.6 | 1.7 ± 0.4 | 0 |
| Example 8 | 6.0 | 2.3 ± 0.3 | 1.9 ± 1 | 10% |
| Example 9 | 3.2 | 8.1 ± 2.3 | 7.2 ± 2.9 | 0 |
| Example 10 | 7.1 | 2.5 ± 0.7 | 2.0 ± 0.9 | 0 |
| Example 11 | 9.4 | 2.8 ± 1.1 | 2.1 ± 1.2 | 0 |
| Example 12 | 6.1 | 2.2 ± 0.5 | 1.2 ± 0.6 | 0 |
| Example 16 | 7.12 | 3.1 ± 0.4 | 2.1 ± 0.5 | 0 |
| Example 17 | 6.0 | 2.2 ± 0.3 | 1.6 ± 0.2 | 0 |
| Example 28 | 1.8 | 3.5 ± 1.1 | 2.1 ± 0.5 | 0 |

[1]Anaesthesia-maintaining time means the time from the abolition of righting reflex to the recovery of righting reflex.
[2]Full recovery time means the time from the recovery of righting reflex to free walk.

Experimental results showed that the placebo didn't produce anesthetic effect, and at the equivalent dose of anesthesia, all compounds including the control drug etomidate, CPMM can immediately anesthetize the rats, and have the rapid-acting characteristic. The maintenance time of anaesthesia of compounds according to the present invention is obviously shorter than that of the control drug etomidate, and after recovery of righting reflex, the standing time of hind legs and the recovery rate of free walk are both more rapid than those of etomidate and CPMM, indicating the wake rate of compounds of the present invention is faster, and the wake quality is better. In addition, for the rats receiving compounds of the application, the incidence rate of muscle tremor is obviously lower than those of rats in etomidate and CPMM groups.

Example 42

30 male SD rats weighing 250~300 g were randomly divided into 6 groups, 5 rats for one group. Compounds of examples 1~9, as well as the control drug etomidate, MOC-ET, and CPMM were prepared as fat emulsions. Each drug was continually infused to rats via caudal vein, and made the righting reflex abolish, and the abolition of righting reflex was maintained for 1 hour. The wake time after drug withdrawal and the time of full recovery were recorded. The results are shown in Table 2.

TABLE 2

Results of sedative effect after continual infusion of compounds of part examples and control drugs.

| Drugs | infusion rate mg/kg/min | Wake time after drug withdrawal[1] (min) | Time of complete recovery[2] (min) | Incidence rate (%) of muscle tremor |
| --- | --- | --- | --- | --- |
| Fat emulsion without drugs | — | — | — | — |
| Etomidate | 0.3 | 18 ± 10 | 85 ± 29 | 60 |
| CPMM | 1 | 12 ± 7 | 25 ± 9 | 90 |
| Example 1 | 6.5 | 2.1 ± 1.1 | 4.1 ± 1.1 | 0 |
| Example 2 | 6.3 | 3.1 ± 1.2 | 3.1 ± 1.8 | 0 |
| Example 3 | 3.0 | 3.4 ± 1.1 | 1.9 ± 0.9 | 0 |
| Example 4 | 1.1 | 25 ± 24 | 90 ± 37 | 20 |
| Example 5 | 3.8 | 6.2 ± 1.2 | 3.9 ± 2.6 | 10 |
| Example 6 | 4.8 | 3.1 ± 1.9 | 2.1 ± 1.5 | 0 |
| Example 8 | 4.2 | 4.9 ± 2.7 | 1.8 ± 0.6 | 10% |
| Example 9 | 0.8 | 20 ± 14 | 55 ± 38 | 0 |
| Example 16 | 4.1 | 4.5 ± 2.2 | 2.1 ± 0.5 | 0 |
| Example 28 | 0.75 | 10.1 ± 2.3 | 22.5 ± 4.8 | 0 |

[1]Wake time after drug withdrawal means the recovery time of righting reflex after discontinuance of drug.
[2]Full recovery time means the time from the recovery of righting reflex to free walk.

It can be shown that for most of compounds of the application, after withdrawal of continual infusion for 1 h, the wake time and the full recovery time of rats are both shorter than those of etomidate, MOC-ET, and CPMM. The recovery quality is better than those of etomidate, MOC-ET, and CPMM. In addition, during anesthesia using compounds of the application, the incidence rate of muscle tremor is obviously lower than those of etomidate, MOC-ET and CPMM.

Example 43

In Vitro Degradation Experiment of Compounds.
Chromatographic condition: mobile phase is methanol: H$_2$O=65:35, and the water phase contains 0.06% ammonium acetate; the flow rate is 1 mL/min; the column temperature is 25° C.

Apparatus: Agilent 1100 Series. Chromatographic column: Aglent Eclipse Plus $C_{18}$ column, 5 μm 4.6*150 nm.

The linear range is 1-50 μg/mL.

After fasting for 24 h, male SD rats were treated to collect liver, and the water on the surface of liver was removed using the filter paper, then liver was weighed. On the ice bath, liver tissue was cut into pieces, and 0.1 mol/l PBS solution was added to prepare 25% hepatic tissue solution, that was smashed to make the liver homogenate. Then, the homogenate was centrifugated at 10000 g for 20 min at the temperature of 4° C. The supernatant solution was collected, and 14 samples (2 mL) of liver homogenate were taken out and warmed to 37° C. in water bath. Each compound (content 10 mg/mL, 10 μl) was added, respectively, to make a concentration of 50 μg/mL in liver homogenate.

At 10, 30, and 60 min, 200 μl sample was collected, respectively, to which was added 400 μl methanol to precipitate. After centrifugation, the supernatant solution was taken out and injected. The concentration of each compound at each time point was detected, that was divided by the initial concentration of each compound, to obtain the degradation ratio of each compound. The result was shown in Table 3.

TABLE 3

The residual ratio of compounds of certain examples in rat liver homogenate at 5, 10, and 20 min.

| Drugs | Residual rate at 5 min (%) | Residual rate at 10 min (%) | Residual rate at 20 min (%) |
|---|---|---|---|
| Etomidate | 97.9 | 95.9 | 95.9 |
| CPMM | 0 | 0 | 0 |
| MOC-ET | 0 | 0 | 0 |
| Example 1 | 0 | 0 | 0 |
| Example 2 | 0 | 0 | 0 |
| Example 3 | 0 | 0 | 0 |
| Example 4 | 89.3 | 60.1 | 43.6 |
| Example 5 | 0 | 0 | 0 |
| Example 6 | 4.7 | 0.9 | 0 |
| Example 8 | 2.1 | 0 | 0 |
| Example 9 | 72.1 | 50.3 | 39.8 |
| Example 16 | 3.2 | 0 | 0 |
| Example 17 | 3.1 | 0 | 0 |
| Example 28 | 5.3 | 0 | 0 |

The result showed that at 5, 10, and 20 min, the residual rate of each compound according to the present invention, as well as MOC-ET and CPMM were all lower than that of control drug etomidate, indicating that the metabolic rate of compounds according to the present invention is obviously faster than that of etomidate, that is beneficial for shortening the clearance time of drug in body after discontinuance of drug, thus reducing the suppression of drug prototype against cortical hormones.

Example 44

Male rats (250~300 g) were chosen as test animals, and the content of corticosterone in serum of rats was measured using ELISA kit and ELISA reader. 65 SD rats were randomly divided into 13 groups, five rats for each group. After dexamethasone (0.2 mg/kg) was administrated respectively, the level of adrenal cortex in body of animal was reduced to the baseline. Subsequently, rats received the equivalent dose of anesthesia induction ($2ED_{50}$) of compounds in examples 1~10, as well as etomidate, MOC-ET, CPMM, and the same volume of solvent DMSO. After 15 min, ACTH (adrenocorticotropic hormone) stimulation was given and made the cortex hormone level in animal body improve. 30 min After administration of ACTH, the concentrations of two cortical hormones in animal body were determined. After drug administration, the improvement of cortical hormone level of animals following ACTH stimulation in each group were shown in Table 4.

TABLE 4

The inhibition of compounds in certain examples on cortical hormones.

| Drugs | The basal concentration of corticosterone (ng/mL) | The concentration of corticosterone after stimulation (ng/mL) |
|---|---|---|
| DMSO | 85.5 ± 29.9 | 301.2 ± 132.4 |
| Etomidate | 77.7 ± 51 | 79.7 ± 69.2 |
| CPMM | 69.7 ± 62.4 | 222.6 ± 85.9 |
| Example 1 | 64.9 ± 43.3 | 287.1 ± 59.6 |
| Example 2 | 44.6 ± 45.2 | 230.3 ± 86.3 |
| Example 3 | 59.5 ± 47.6 | 347.2 ± 169.4 |
| Example 5 | 103.8 ± 36.4 | 279.1 ± 155.4 |
| Example 6 | 70.9 ± 36.7 | 309.5 ± 81.6 |
| Example 8 | 57.2 ± 38.5 | 314.9 ± 97.6 |
| Example 9 | 85.6 ± 27.7 | 216.8 ± 83.1 |
| Example 10 | 78.3 ± 71.1 | 356.0 ± 135.8 |
| Example 17 | 50.3 ± 28.6 | 300.1 ± 87.9 |
| Example 28 | 61.2 ± 30.1 | 289.6 ± 77.9 |

Above experimental result showed that etomidate could significantly suppress the self-synthesis of adrenal cortical hormones, and make the cortex level can not be improved by stimulation of ACTH. While for most of compounds of the application, CPMM, and MOC-ET, the cortex function of test animals can be obviously recovered 30 min after drug withdrawal, that was displayed by obvious increase of corticoid level in animals via ACTH stimulation, and the increase was same to that of blank control group.

The invention claimed is:

1. An N-substituted imidazole carboxylate compound of formula (I) and a pharmaceutically acceptable salt thereof,

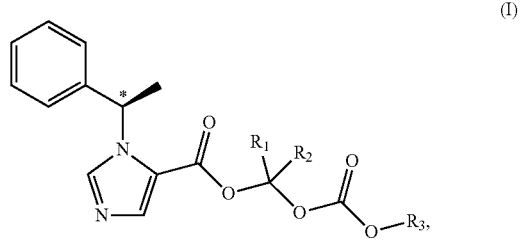

(I)

in formula (I), C* is an R-type chiral carbon atom, $R_1$ and $R_2$ are independently selected from H, methyl, ethyl, cyclopropyl, cyclobutyl, and isopropyl, or $R_1$ and $R_2$ form a $C_{2-5}$ alkylenyl group; $R_3$ is a substituted or unsubstituted $C_{1-18}$ saturated or unsaturated aliphatic hydrocarbon or aromatic hydrocarbon, in which the aliphatic hydrocarbon comprises a straight chain, branched chain or cyclic aliphatic hydrocarbyl.

2. The N-substituted imidazole carboxylate compound according to claim 1, wherein, in formula (I), $R_3$ is substituted by halogen, nitro, or aryl.

3. The N-substituted imidazole carboxylate compound according to claim 1, wherein, in formula (I), $R_1$ is hydrogen, $R_2$ is hydrogen, $R_3$ is methyl, ethyl, n-propyl, isopropyl, isobutyl, sec-butyl, tert-butyl, neopentyl, cyclobutyl, 3-methyl-2-butyl, phenyl, or p-bromophenyl; or in formula (I), $R_1$ and $R_2$ form ethylene, $R_3$ is methyl, ethyl, or isopropyl; or in formula (I), $R_1$ is methyl, $R_2$ is hydrogen, $R_3$ is methyl, ethyl, isopropyl, or sec-butyl; or in formula (I), $R_1$ is methyl, $R_2$ is methyl, $R_3$ is methyl, ethyl, or isopropyl; or in formula (I), $R_1$ is ethyl, $R_2$ is hydrogen, $R_3$ is methyl, ethyl, or isopropyl; or in formula (I), $R_1$ is isopropyl, $R_2$ is hydrogen, $R_3$ is methyl, ethyl, or isopropyl; or in formula (I), $R_1$ is cyclopropyl, $R_2$ is hydrogen, $R_3$ is methyl, ethyl, or isopropyl; or in formula (I), $R_1$ is cyclobutyl, $R_2$ is hydrogen, $R_3$ is methyl, ethyl, or isopropyl; or in formula (I), $R_1$ is hydrogen, $R_2$ is hydrogen, $R_3$ is difluoroethyl, hexafluoroisopropyl, trifluoroethyl or nitroethyl; or in formula (I), $R_1$ is hydrogen, $R_2$ is hydrogen, $R_3$ is 2-methyl-3-buten-2-yl or isopentenyl.

4. The pharmaceutically acceptable salt according to claim 1 which is a sulfonate or a hydrochlorate of the compound of formula (I).

5. The preparative method of N-substituted imidazole carboxylate compound according to claim 1, comprising:
reacting an N-substituted imidazole carboxylic compound of formula (II) and a halogenated compound of formula (III) in presence of a base:

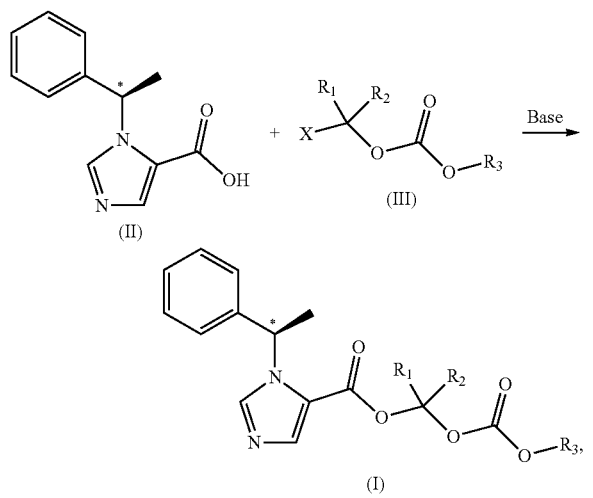

wherein X is a halogen atom.

6. The preparative method according to claim 5, wherein X is chlorine.

7. The preparative method according to claim 5, wherein the base is selected from potassium carbonate, cesium carbonate, triethylamine, 1,8-diazabicycloundec-7-ene, and mixtures thereof.

8. The preparative method according to claim 5, wherein the reaction is carried out in a polar aprotic solvent.

9. The preparative method according to claim 8, wherein the polar aprotic solvent is N,N-dimethylformamide, dimethylsulfoxide, or acetonitrile.

10. The preparative method of the N-substituted imidazole carboxylate compound according to claim 1, comprising reacting an N-substituted imidazole carboxylic compound of formula (IV) and a chloroformate compound of formula (V) to obtain the compound of formula (I):

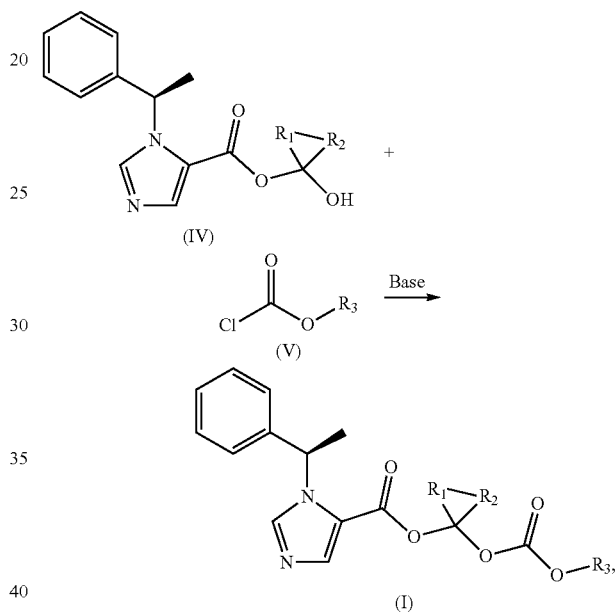

wherein $R_1$ and $R_2$ form a C2-5 alkylenyl group.

11. A central inhibitory drug, comprising the N-substituted imidazole carboxylate compound and the pharmaceutically acceptable salt thereof according to claim 1.

12. A method for inducing anesthetic effect in a subject in need thereof, comprising administering to the subject the N-substituted imidazole carboxylate compound and the pharmaceutically acceptable salt thereof according to claim 1.

* * * * *